(12) United States Patent
Kawada et al.

(10) Patent No.: US 6,528,074 B2
(45) Date of Patent: Mar. 4, 2003

(54) LIPID COMPOSITION CONTAINING A LIQUID CRYSTAL STRUCTURE

(75) Inventors: Izumi Kawada, Kanagawa (JP); Kenya Ishida, Kanagawa (JP); Kiyohito Sawano, Kanagawa (JP); Toshimitsu Hagiwara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/874,312

(22) Filed: Jun. 6, 2001

(65) Prior Publication Data

US 2002/0012649 A1 Jan. 31, 2002

(30) Foreign Application Priority Data

Jun. 6, 2000 (JP) ........................................ 2000-169104

(51) Int. Cl.[7] ..................... A61K 7/00; C07C 231/00; C07C 233/00
(52) U.S. Cl. ..................... 424/401; 564/135; 564/203
(58) Field of Search ........................... 424/401; 564/203, 564/135

(56) References Cited

U.S. PATENT DOCUMENTS

| | | | |
|---|---|---|---|
| 5,372,814 A | * 12/1994 | Mizushima et al. | 424/401 |
| 5,831,125 A | * 11/1998 | Sakurai et al. | 564/135 |
| 5,916,578 A | 6/1999 | Kawada et al. | 424/401 |
| 5,998,668 A | * 12/1999 | Sakurai et al. | 564/203 |

FOREIGN PATENT DOCUMENTS

| | | |
|---|---|---|
| EP | 0 278 505 B1 | 8/1988 |
| EP | 0716849 A1 | 6/1996 |
| EP | 0728473 A1 | 8/1996 |
| EP | 0875232 A1 | 11/1998 |
| EP | 0856510 A1 | 6/1999 |
| EP | 0 920 852 | * 6/1999 |
| EP | 0920852 A2 | 6/1999 |
| JP | 9-235259 | * 9/1997 |
| JP | 2000-264826 | * 9/2000 |
| WO | WO 99/29293 | * 6/1999 |
| WO | WO 99/29293 A1 | 6/1999 |

OTHER PUBLICATIONS

European Search Report, Oct. 18, 2001.
Philip W. Wertz et al., Preparation of Liposomes From Stratum Corneum Lipids, vol. 17, The Journal of Investigative Dermatology, pp. 582–584 (1986).
M. Philippe et al., Synthesis of 2–N–oleoylamino–octadecane–1,3–diol: A New Ceramide Highly Effective for the Treatment of Skin and Hair, Int'l Journal of Cosmetic Science, vol. 17, pp. 133–146 (1995).
G. Hussler et al., Isolation and Identification of Human Hair Ceramides, Int'l Journal of Cosmetic Science, vol. 17, pp. 197–206 (1995).

* cited by examiner

*Primary Examiner*—Sreeni Padmanabhan
*Assistant Examiner*—Michael A. Willis
(74) *Attorney, Agent, or Firm*—Sughrue Mion, PLLC (57) ABSTRACT

This invention relates to a novel lipid composition for use in cosmetics capable of increasing moisture-keeping ability or barrier function of the stratum corneum, protecting the skin and improving dry or rough skin, and to products which use the same, such as cosmetics and medicaments. Particularly, it relates to a lipid composition which comprises at least one component (A) selected from the group consisting of a 2-acylaminoalkane-1,3-diol and optically active compounds thereof, at least one component (B) selected from the group consisting of a 2-acylaminoalkane-1,3-diol in which at least one of the $\alpha$-position and $\beta$-position of the acyl group is substituted with hydroxyl group and optically active compounds thereof and at least one component (C) selected from sterols, wherein the components (A), (B) and (C) are mixed at a ratio that constructs a liquid crystal structure, and to products which contain the lipid composition, such as cosmetics and medicaments.

6 Claims, 2 Drawing Sheets

LIPID COMPOSITION CONTAINING A LIQUID CRYSTAL STRUCTURE

FIELD OF THE INVENTION

This invention relates to a novel composition having a liquid crystal structure, and in particular, to a mixture of compounds belonging to the ceramide family, sterol family and a medium suitable for cosmetics or medicaments.

DESCRIPTION OF THE RELATED ART

In order to keep smooth skin by adding moisture to the skin and inhibiting abnormal transpiration of moisture from the skin, it is considered that moisture-keeping ability of the stratum corneum of the skin has an important role. Moisture in the stratum corneum contains many water-soluble components such as free amino acids, organic acids, urea and inorganic ions, and they are considered to be concerned in the moisture-keeping of the stratum corneum, so that these substances are practically used for the purpose of improving or preventing dry or rough skin by adding them alone or in combination to cosmetics and external drug preparations for skin use.

Recently, it has been revealed that intercellular lipids in the stratum corneum control transpiration of moisture from the body and keep softness and smoothness of the skin by preventing invasion of stimulants from the outside.

The intercellular lipids are composed of a ceramide as the main component and other components such as cholesterol sulfate, palmitic acid and cholesterol. Regarding a ceramide which corresponds to a racemic compound of general formula (II) that will be described later, preparation of a ceramide composition mixed with the same components described above is disclosed in JP-A-4-327563 (the term "JP-A" as used herein means an "unexamined published Japanese patent application").

It has been confirmed that such an intercellular lipid in stratum corneum or ceramide composition has high moisture-keeping ability. Taking these circumstances into consideration, ceramides such as racemic ceramide, pseudoceramide and glycosyl ceramide have recently been obtained by certain means such as chemical synthesis or extraction from natural materials, and, with the aim of improving conditions of the skin, studies have been positively conducted on the application of foundation cosmetics and medicaments mixed with a lipid composition containing these components to the improvement of dry or rough skin.

Since ceramide is hardly soluble in water or organic solvents, for the purpose of applying ceramide to the skin, it is necessary to use it by firstly preparing a lipid composition having a specified mixing ratio so as to form a lamellar liquid crystal structure, and then effect formation of a lamellar liquid crystal phase and then converting the composition into the form of a cosmetic or medicament by adding pharmacologically acceptable base materials and fillers which do not destroy the liquid crystal phase.

It is considered that intercellular lipid in the stratum corneum is composed of a ceramide as the main component and other components such as cholesterol sulfate, palmitic acid and cholesterol, and their mixture generally forms a lamellar liquid crystal structure.

However, according to the report by Wertz, P. W. et al., uniform lamellar liquid crystal structure cannot be formed from ceramide alone or a mixture of ceramide and cholesterol (Wertz, P. W. et al., *J. Invest. Dermatol*, vol. 87, p. 582 (1986)).

There is a report to recommend a hair protecting composition containing either ceramide or glycosyl ceramide and at least one kind of cholesterol ester (Japanese Patent 2,510,235).

According to another study, it has been reported that a lipid component was selected from the group consisting of a ceramide, a pseudoceramide, a polyester consisting of a polyol and a fatty acid, a phospholipid, a galactosyldiacylglycerol, a sphingoglycolipid, a derivative of succinic acid and a mixture thereof was used to cure xeroderma (JP-A-8-157283).

Also, there is a report stating that a mixture comprised of a composition having a liquid crystal structure, an amphoteric and/or semi-polar surface active agent, a higher fatty acid and water was prepared and made into a composition which shows excellent cosmetic durability and can improve water resistance and sebum resistance (JP-A-8-217633).

In addition to the above, with the aim of obtaining cosmetics, quasi-drugs or medicaments for use in preventing dry and rough skin, keeping skin moisture to make smooth skin and preventing aged skin, various attempts have been made to apply liquid crystal composed of ceramides and other components such as fatty acids, cholesterol, cholesterol esters, polyhydric alcohols or various lipids.

Their examples include a cosmetic for smooth skin use prepared from a liquid crystal emulsion obtained by heating and mixing at least one compound selected from ceramide, glycosyl ceramide and galactosyl ceramide with cholesterol, a fatty acid, a water-soluble polyhydric alcohol and an aqueous medium (JP-A-7-303473), a liquid crystal skin cosmetic or emulsified skin cosmetic having an effect to prevent or improve dry and rough skin, in which one or more compounds selected from ceramide and a substance having a structure analogous to ceramide, one or more compounds selected from alkylpolyglucosides and one or more compounds selected from alcohols and polyols are formulated (JP-A-9-157149), a cosmetic composition which contains a ceramide-like compound and can delay aging of skin (JP-A-10-226674) and a skin cosmetic having a liquid crystal structure in which a cholesterol ester of an iso or anteiso fatty acid, α-hydroxy acid and sphingolipids such as sphingoglycolipid and sphingophospholipid are formulated (JP-A-11-60461).

In a general way, it is considered that the ceramide or glycosyl ceramide used in each of the above reports is preferably a natural type ceramide rather than a non-natural synthetic ceramide. The natural type ceramide mainly used to date has been obtained from materials such as swine skin, bovine brain, plants and cultured fungi, but they are not satisfactory for users from the viewpoint of purity, cost or unstable supply due to epidemic diseases (e.g., bovine spongiform encephalopathy) of animals to be used.

Under such circumstances, studies on the synthesis of natural type optically active ceramides have been carried out and their supply at an industrial level became possible (JP-A-9-235329).

Among these studies, a lipid composition having a lamellar liquid crystal structure, prepared by formulating a ceramide obtained by chemical synthesis and/or an optical isomer thereof, has been proposed (JP-A-11-12118).

According to this invention, however, the lipid composition is a mixture of four compounds (ceramide, acetylsphinganine, a fatty acid or cholesterol ester and cholesterol), so that it has been required not only to make a lipid composition more simple formulation, but also to show further improved function or performance.

Thus, the invention contemplates providing a lipid composition which can improve dry or rough skin and accompanying diseases by increasing moisture-keeping ability of the stratum corneum to a level higher than the conventional compositions through simple formulation and also providing a cosmetic or medicament containing this lipid composition. This cosmetic or medicament has higher ability to protect the skin from drying by adding appropriate moisture, in comparison with its counterparts in which the conventional lipid compositions are formulated.

SUMMARY OF THE INVENTION

With the aim of achieving these objects, the present inventors have conducted intensive studies and found as a result of the efforts that a lipid composition shown below, namely a lipid composition comprised of two types of synthetic ceramide and cholesterol, forms a lamellar liquid crystal structure by a blending ratio described in the following. The invention has been accomplished based on this finding.

The lipid composition of the invention is comprised of a racemic 2-acylaminoalkane-1,3-diol or an optically active compound thereof, a racemic 2-acylaminoalkane-1,3-diol having an acyl group in which at least one of the α-position and β-position is substituted with hydroxyl group or an optically active compound thereof and sterols.

This composition can further contain a pharmaceutically acceptable base material or filler. Such a composition is suitably used particularly in, e.g., cosmetics, external skin protection preparations and bath additives.

This composition can keep moisture in those to which it is applied, and when applied to the skin, it prevents abnormal transpiration of moisture from the skin and also adds appropriate humidity to the skin. Thus, the composition of the invention can protect the skin from drying and its appropriate formulation can provide, e.g., desirable cosmetics, external skin protection preparations or bath additives.

Accordingly, the invention is described as follows.

1. A lipid composition which comprises (1) at least one component (A) selected from the group consisting of a 2-acylaminoalkane-1,3-diol represented by a general formula (I)

(I)

(wherein $R^1$ represents a straight chain alkyl group having from 9 to 17 carbon atoms and $R^2$ represents a straight chain acyl group having from 14 to 24 carbon atoms) and optically active compounds thereof, (2) at least one component (B) selected from the group consisting of a 2-acylaminoalkane-1,3-diol represented by a general formula (II)

(II)

(wherein $R^1$ represents a straight chain alkyl group having from 9 to 17 carbon atoms and $R^3$ represents a straight chain acyl group having from 2 to 24 carbon atoms in which at least one of the α-position and β-position is substituted with hydroxyl group) and optically active compounds thereof and (3) at least one component (C) selected from sterols, wherein the components (A), (B) and (C) are mixed at a ratio that constructs a liquid crystal structure.

2. The lipid composition having a liquid crystal structure according to the above item 1, wherein the sterols of component (C) is cholesterol.

3. The lipid composition having a liquid crystal structure according to the above item 1 or 2, wherein the component (A) is a (2S,3R)-2-acylaminoalkane-1,3-diol represented by a general formula (III)

(III)

(wherein $R^1$ and $R^2$ are as defined in the foregoing).

4. The lipid composition having a liquid crystal structure according to any one of the above items 1 to 3, wherein the component (B) is a (2S,3R)-2-acylaminoalkane-1,3-diol represented by a general formula (IV)

(IV)

(wherein $R^1$ and $R^3$ are as defined in the foregoing).

5. The lipid composition having a liquid crystal structure according to any one of the above items 1 to 4, wherein $R^3$ of the component (B) is an acyl group in which the α-position carbon of β-position carbon is substituted with hydroxyl group.

6. The lipid composition having a liquid crystal structure according to any one of the above items 1 to 5, wherein weight ratios of the component (A) to component (B), component (B) to component (C) and component (A) to component (C) are within the range of from 1:9 to 9:1, from 9:6 to 1:10 and from 1:1 to 1:9, respectively.

7. A cosmetic or medicament which comprises the lipid composition defined in any one of the above items 1 to 6 containing a pharmaceutically acceptable base material as an additional component.

Other objects and advantages of the invention will be made apparent as the description progresses.

DETAILED DESCRIPTION OF THE INVENTION

The 2-acylaminoalkane-1,3-diols to be used in the invention can be prepared by chemical synthesis. These compounds may be in the form of racemic bodies, natural type optically active isomers, non-natural type optically active isomers or mixtures thereof.

$R^1$ of the 2-acylaminoalkane-1,3-diol of component (A) is a straight chain alkyl group having from 9 to 17 carbon atoms, typically a straight chain alkyl group having 15 carbon atoms. Also, $R^2$ is a straight chain acyl group having from 14 to 24 carbon atoms, typically an acyl group having 18 carbon atoms.

Regarding the 2-acylaminoalkane-1,3-diol as the component (A) represented by the general formula (I), its examples particularly in which $R^1$ has 15 carbon atoms include:
2-tetradecanoylaminooctadecane-1,3-diol,
2-pentadecanoylaminooctadecane-1,3-diol,
2-hexadecanoylaminooctadecane-1,3-diol,
2-heptadecanoylaminooctadecane-1,3-diol,
2-octadecanoylaminooctadecane-1,3-diol,
2-nonadecanoylaminooctadecane-1,3-diol and
2-eicosanoylaminooctadecane-1,3-diol, though not limited thereto.

$R^1$ of the 2-acylaminoalkane-1,3-diol of component (B) is a straight chain alkyl group having from 9 to 17 carbon atoms, typically, $R^1$ is a straight chain alkyl group having 15 carbon atoms. Also, $R^3$ of the component is a straight chain acyl group having from 2 to 24 carbon atoms in which at least one position is substituted with hydroxyl group, typically, $R^3$ is an acyl group having 16 carbon atoms in which one hydrogen atom on the 2-position carbon atom of the acyl group is substituted by hydroxyl group.

Regarding the 2-acylaminoalkane-1,3-diol as the component (B) represented by the general formula (II), its examples particularly in which $R^1$ has 15 carbon atoms include:
2-(2-hydroxyethanoyl)aminooctadecane-1,3-diol,
2-(2-hydroxypropanoyl)aminooctadecane-1,3-diol,
2-(2-hydroxybutanoyl)aminooctadecane-1,3-diol,
2-(2-hydroxypentanoyl)aminooctadecane-1,3-diol,
2-(2-hydroxyhexanoyl)aminooctadecane-1,3-diol,
2-(2-hydroxyheptanoyl)aminooctadecane-1,3-diol,
2-(2-hydroxyoctanoyl)aminooctadecane-1,3-diol,
2-(3-hydroxyoctanoyl)aminooctadecane-1,3-diol,
2-(2-hydroxynonanoyl)aminooctadecane-1,3-diol,
2-(2-hydroxydecanoyl)aminooctadecane-1,3-diol,
2-(3-hydroxydecanoyl)aminooctadecane-1,3-diol,
2-(2-hydroxyundecanoyl)aminooctadecane-1,3-diol,
2-(2-hydroxydodecanoyl)aminooctadecane-1,3-diol,
2-(2-hydroxytridecanoyl)aminooctadecane-1,3-diol,
2-(2-hydroxytetradecanoyl)aminooctadecane-1,3-diol,
2-(2-hydroxypentadecanoyl)aminooctadecane-1,3-diol,
2-(2-hydroxyhexadecanoyl)aminooctadecane-1,3-diol,
2-(2-hydroxyheptadecanoyl)aminooctadecane-1,3-diol,
2-(2-hydroxyoctadecanoyl)aminooctadecane-1,3-diol,
2-(2-hydroxynonadecanoyl)aminooctadecane-1,3-diol and
2-(2-hydroxyeicosanoyl)aminooctadecane-1,3-diol, though not limited thereto.

The optically active (2S,3R)-2-acylaminoalkane-1,3-diols having (2S,3R)-configuration, as the component (A) and component (B) to be used in the invention, can be produced by known methods (JP-A-9-235259, JP-A-10-218851). Among compounds represented by the general formulae (III) and (IV), the optically active (2S,3R)-2-acylaminooctadecane-1,3-diol as a compound in which $R^1$ has 15 carbon atoms can be produced by carrying out acylation of (2S,3R)-2-aminooctadecane-1,3-diol obtained in accordance with the methods described in JP-A-6-80617 and JP-A-9-176097, using an appropriate acylation agent.

That is, a 2-acetamino-3-oxooctadecanoic acid ester is prepared in accordance with the method of D. Shapiro et al. (*J. Am. Chem. Soc.*, 80, 2170 (1958). Next, the 2-acetamino-3-oxooctadecanoic acid ester is subjected to asymmetric hydrogenation using a ruthenium-optically active phosphine complex (in this case, (−)-form optically active phosphine complex is used) as the catalyst, and then thionyl chloride is allowed to react with the thus obtained optically active (2R,3S)-2-acetamino-3-hydroxyoctadecanoic acid ester to effect reversion of the configuration of hydroxyl group and to thereby obtain (2R,3R)-2-acetamino-3-hydroxyoctadecanoic acid ester. Next, optically active (2S,3R)-2-acetaminooctadecane-1,3-diol is obtained by reducing only the ester moiety using sodium borohydride. Thereafter, (2S,3R)-2-aminooctadecane-1,3-diol is obtained by hydrolyzing the acetyl group with an acid or alkali and then subjected to acylation using an appropriate acylation agent to obtain the optically active (2S,3R)-2-acylaminooctadecane-1,3-diols of components (A) and (B).

Examples of the acylation agent to be used include commercially available higher fatty acids, higher fatty acid esters, higher fatty acid halides, higher fatty acid anhydrides, higher fatty acid anhydrides mixtures, higher fatty acid p-nitrophenyl esters and higher fatty acid N-hydroxysuccinimide esters. Their illustrative examples include tetradecanoic acid, tridecanoic acid, pentadecanoic acid, hexadecanoic acid, heptadecanoic acid, octadecanoic acid, nonadecanoic acid, eicosanoic acid, 2-hydroxytetradecanoic acid, 2-hydroxytridecanoic acid, 2-hydroxypentadecanoic acid, 2-hydroxyhexadecanoic acid, 2-hydroxyheptadecanoic acid, 2-hydroxyoctadecanoic acid, 2-hydroxynonadecanoic acid, 2-hydroxyeicosanoic acid and 3-hydroxyhexadecanoic acid, and lower esters, acid chlorides, acid anhydrides, acid mixture anhydrides, acid p-nitrophenyl esters and acid N-hydroxysuccinimide esters of acids derived from these fatty acids.

In addition, the racemic 2-acylaminoalkane-1,3-diol can be obtained by carrying out acylation of 2-aminooctadecane-1,3-diol obtained by the method of D. Shapiro et al. (*J. Am. Chem. Soc.*, 80, 2170 (1958), using an appropriate acylation agent described above.

$R^1$ of the optically active compound (2S,3R)-2-acylaminoalkane-1,3-diol of component (A) represented by the general formula (III) is a straight chain alkyl group having from 9 to 17 carbon atoms, typically, $R^1$ is a straight chain alkyl group having 15 carbon atoms. Also, $R^2$ of this component is a straight chain acyl group having from 14 to 24 carbon atoms, typically an acyl group having 18 carbon atoms.

Regarding the (2S,3R)-2-acylaminoalkane-1,3-diol as the component (A) represented by the general formula (III), its examples particularly in which $R^1$ has 15 carbon atoms include:
(2S,3R)-2-tetradecanoylaminooctadecane-1,3-diol,
(2S,3R)-2-pentadecanoylaminooctadecane-1,3-diol,
(2S,3R)-2-hexadecanoylaminooctadecane-1,3-diol,
(2S,3R)-2-heptadecanoylaminooctadecane-1,3-diol,
(2S,3R)-2-octadecanoylaminooctadecane-1,3-diol,
(2S,3R)-2-nonadecanoylaminooctadecane-1,3-diol and
(2S,3R)-2-eicosanoylaminooctadecane-1,3-diol, though not limited thereto.

$R^1$ of the optically active compound (2S,3R)-2-acylaminoalkane-1,3-diol of component (B) represented by the general formula (IV) is an alkyl group having from 9 to 17 carbon atoms, typically, $R^1$ is an alkyl group having 15 carbon atoms. Also, $R^3$ of the component is a straight chain acyl group having from 2 to 24 carbon atoms (preferably 14 to 24 carbon atoms) in which at least one position of the α-position and β-position of the acyl group is substituted with hydroxyl group, typically, $R^3$ is an acyl group having 16 carbon atoms in which the α-position of acyl group is substituted by hydroxyl group.

Regarding the optically active compound (2S,3R)-2-acylaminoalkane-1,3-diol as the component (B) represented by the general formula (IV), its examples particularly in which $R^1$ has 15 carbon atoms include:
(2S,3R)-2-(2-hydroxyethanoyl)aminooctadecane-1,3-diol,
(2S,3R)-2-(2-hydroxypropanoyl)aminooctadecane-1,3-diol,
(2S,3R)-2-(2-hydroxybutanoyl)aminooctadecane-1,3-diol,
(2S,3R)-2-(2-hydroxypentanoyl)aminooctadecane-1,3-diol,
(2S,3R)-2-(2-hydroxyhexanoyl)aminooctadecane-1,3-diol,
(2S,3R)-2-(2-hydroxyheptanoyl)aminooctadecane-1,3-diol,
(2S,3R)-2-(2-hydroxyoctanoyl)aminooctadecane-1,3-diol,
(2S,3R)-2-(3-hydroxyoctanoyl)aminooctadecane-1,3-diol,
(2S,3R)-2-(2-hydroxynonanoyl)aminooctadecane-1,3-diol,
(2S,3R)-2-(2-hydroxydecanoyl)aminooctadecane-1,3-diol,
(2S,3R)-2-(3-hydroxydecanoyl)aminooctadecane-1,3-diol,
(2S,3R)-2-(2-hydroxyundecanoyl)aminooctadecane-1,3-diol,
(2S,3R)-2-(2-hydroxydodecanoyl)aminooctadecane-1,3-diol,
(2S,3R)-2-(2-hydroxytridecanoyl)aminooctadecane-1,3-diol,
(2S,3R)-2-(2-hydroxytetradecanoyl)aminooctadecane-1,3-diol,
(2S,3R)-2-(2-hydroxypentadecanoyl)aminooctadecane-1,3-diol,
(2S,3R)-2-(2-hydroxyhexadecanoyl)aminooctadecane-1,3-diol,
(2S,3R)-2-(3-hydroxyhexadecanoyl)aminooctadecane-1,3-diol,
(2S,3R)-2-(2-hydroxyheptadecanoyl)aminooctadecane-1,3-diol,
(2S,3R)-2-(2-hydroxyoctadecanoyl)aminooctadecane-1,3-diol,
(2S,3R)-2-(2-hydroxynonadecanoyl)aminooctadecane-1,3-diol and
(2S,3R)-2-(2-hydroxyeicosanoyl)aminooctadecane-1,3-diol, as well as
(2S,3R,2'S)-2-(2'-hydroxyethanoyl)aminooctadecane-1,3-diol,
(2S,3R,2'R)-2-(2'-hydroxypropanoyl)aminooctadecane-1,3-diol,
(2S,3R,2'S)-2-(2'-hydroxybutanoyl)aminooctadecane-1,3-diol,
(2S,3R,2'R)-2-(2'-hydroxypentanoyl)aminooctadecane-1,3-diol,
(2S,3R,2'S)-2-(2'-hydroxyhexanoyl)aminooctadecane-1,3-diol,
(2S,3R,2'R)-2-(2'-hydroxyheptanoyl)aminooctadecane-1,3-diol,
(2S,3R,2'R)-2-(2'-hydroxyoctanoyl)aminooctadecane-1,3-diol,
(2S,3R,3'R)-2-(3'-hydroxyoctanoyl)aminooctadecane-1,3-diol,
(2S,3R,2'R)-2-(2'-hydroxynonanoyl)aminooctadecane-1,3-diol,
(2S,3R, 2'R)-2-(2'-hydroxydecanoyl)aminooctadecane-1,3-diol,
(2S,3R,2'S)-2-(2'-hydroxydecanoyl)aminooctadecane-1,3-diol,
(2S,3R,2'R)-2-(3'-hydroxydecanoyl)aminooctadecane-1,3-diol,
(2S,3R,2'R)-2-(2'-hydroxyundecanoyl)aminooctadecane-1,3-diol,
(2S,3R,2'R)-2-(2'-hydroxydodecanoyl)aminooctadecane-1,3-diol,
(2S,3R,2'S)-2-(2'-hydroxydodecanoyl)aminooctadecane-1,3-diol,
(2S,3R,3'R)-2-(3'-hydroxydodecanoyl)aminooctadecane-1,3-diol,
(2S,3R,2'R)-2-(2'-hydroxytridecanoyl)aminooctadecane-1,3-diol,
(2S,3R,2'R)-2-(2'-hydroxytetradecanoyl)aminooctadecane-1,3-diol,
(2S,3R,2'R)-2-(2'-hydroxypentadecanoyl)aminooctadecane-1,3-diol,
(2S,3R,2'R)-2-(2'-hydroxyhexadecanoyl)aminooctadecane-1,3-diol,
(2S,3R,3'R)-2-(3'-hydroxyhexadecanoyl)aminooctadecane-1,3-diol,
(2S,3R,2'S)-2-(2'-hydroxyhexadecanoyl)aminooctadecane-1,3-diol,
(2S,3R,2'R)-2-(2'-hydroxyheptadecanoyl)aminooctadecane-1,3-diol,
(2S,3R,2'R)-2-(2'-hydroxyoctadecanoyl)aminooctadecane-1,3-diol,
(2S,3R,2'R)-2-(2'-hydroxynonadecanoyl)aminooctadecane-1,3-diol and
(2S,3R,2'R)-2-(2'-hydroxyeicosanoyl)aminooctadecane-1,3-diol, though not limited thereto.

Examples of the sterols to be used in the invention include cholesterol, coprostanol, sitosterol, stigmasterol and ergosterol, of which cholesterol is most desirable. The cholesterol may be either animal or plant origin or a high purity commercial product obtained by chemical synthesis (e.g., Cholesterol mfd. by Wako Pure Chemical Industries).

In order to effect formation of a lamellar liquid crystal structure, the lipid composition of the invention is uniformly stirred by heating to the melting point or more and then gradually cooled. The lipid composition is mixed with water, uniformly stirred by heating to the melting point or more and cooled, and then freezing and thawing are repeated. Also, a liquid crystal phase can be formed by dissolving the composition in a solvent and adding water thereto. In addition, it is possible to form a liquid crystal phase by other methods. The lipid composition of the invention can correspond to any product containing a lamellar liquid crystal phase regardless of the liquid crystal phase formation method.

In a strict sense, suitable mixing ratio of the components (A), (B) and (C) for effecting formation of the liquid crystal structure may vary depending on the kind and purity of each component to be used. However, the mixing ratio can be easily determined by specifying and evaluating kinds and ratios of these components.

In order to construct the lamellar liquid crystal structure of the invention, it is necessary to mix the three components (A), (B) and (C) appropriately, and it is difficult to construct stable lamellar liquid crystal structure when any one of these three components is absent.

When the three components, e.g., (2S,3R)-2-octadecanoylaminooctadecane-1,3-diol as the component (A), (2S,3R)-2-(2-hydroxyhexadecanoyl)aminooctadecane-1,3-diol as the component (B) and cholesterol as the component (C), are used, weight ratios of the (component A) to (component B), (component B) to (component C) and (component A) to (component C) are; (component A):(component B) is from 1:9 to 9:1, preferably from 1:4 to 4:1, (component B):(component C) is from 9:6 to 1:10, preferably from 1:1 to 1:4 and (component A):(component C) is from 1:1 to 1:9, preferably from 1:1 to 1:3, respectively.

When (2S,3R)-2-hexadecanoylaminooctadecane-1,3-diol is used as the component (A), and (2S,3R)-2-(2-hydroxyoctadecanoyl)aminooctadecane-1,3-diol as the component (B) and cholesterol as the component (C), component (A):component (B) is from 1:9 to 9:1, preferably from 1:3 to 4:1, component (B):component (C) is from 9:6 to 1:10, preferably from 1:1 to 1:4 and component (A):component (C) is from 1:1 to 1:9, preferably from 1:1 to 1:3.

When (2S,3R)-2-octadecanoylaminooctadecane-1,3-diol is used as the component (A), and (2S,3R,2'R)-2-(2'-hydroxyhexadecanoyl)aminooctadecane-1,3-diol as the component (B) and cholesterol as the component (C), component (A):component (B) is from 1:9 to 9:1, preferably from 1:3 to 4:1, component (B):component (C) is from 9:6 to 1:10, preferably from 1:1 to 1:4 and component (A):component (C) is from 1:1 to 1:9, preferably from 1:1 to 1:3.

When (2S,3R)-2-tetradecanoylaminooctadecane-1,3-diol is used as the component (A), and (2S,3R,2'R)-2-(2'-hydroxyhexadecanoyl)aminooctadecane-1,3-diol as the component (B) and cholesterol as the component (C), component (A):component (B) is from 1:9 to 9:1, preferably from 1:3 to 4:1, component (B):component (C) is from 9:6 to 1:10, preferably from 1:1 to 1:4 and component (A):component (C) is from 1:1 to 1:9, preferably from 1:1 to 1:3.

When racemic 2-octadecanoylaminooctadecane-1,3-diol is used as the component (A), and (2S,3R)-2-(2-hydroxyhexadecanoyl)aminooctadecane-1,3-diol as the component (B) and cholesterol as the component (C), component (A):component (B) is from 1:9 to 9:1, preferably from 1:3 to 4:1, component (B):component (C) is from 9:6 to 1:10, preferably from 1:1 to 1:3 and component (A):component (C) is from 1:1 to 1:9, preferably from 1:1 to 1:3.

When racemic 2-hexadecanoylaminooctadecane-1,3-diol is used as the component (A), and racemic 2-(2-hydroxyhexadecanoyl)aminooctadecane-1,3-diol as the component (B) and cholesterol as the component (C), component (A):component (B) is from 1:9 to 9:1, preferably from 1:3 to 4:1, component (B):component (C) is from 9:6 to 1:10, preferably from 1:1 to 1:4 and component (A):component (C) is from 1:1 to 1:9, preferably from 1:1 to 1:3.

For example, stable lamellar liquid crystal structure can be formed when (2S,3R)-2-octadecanoylaminooctadecane-1,3-diol (component A), (2S,3R)-2-(2-hydroxyhexadecanoyl)aminooctadecane-1,3-diol (component B) and cholesterol (component C) are mixed at a ratio of 1:1:1, 1:2:3 or 4:1:4.

Figure 1:
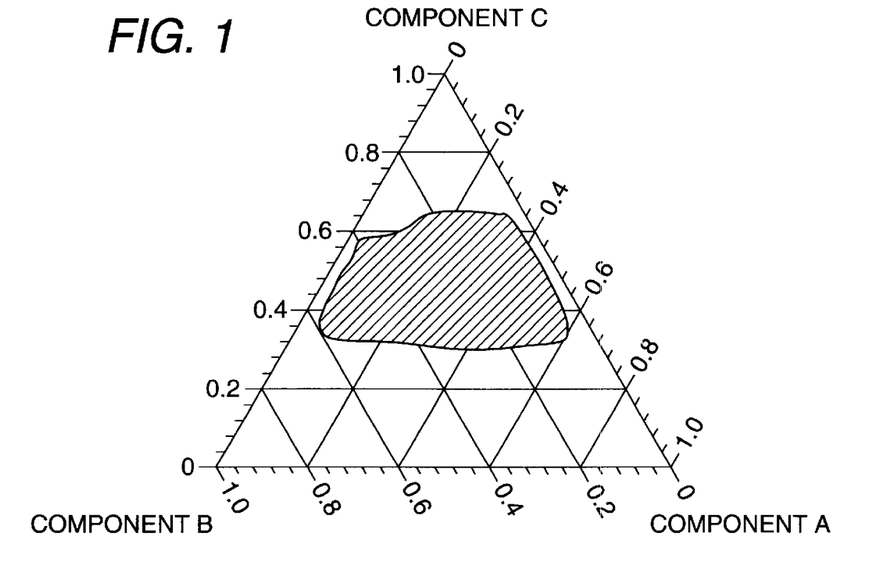
FIG. 1 is a graph showing a ternary phase equilibrium diagram comprised of (2S,3R)-2- octadecanoylaminooctadecane-1,3-diol (A), (2S,3R)-2-(2-hydroxyhexadecanoyl)aminooctadecane-1,3-diol (B) and cholesterol (C).

FIG. 1 is a graph showing ternary phase equilibrium diagram of a mixture of three compounds (2S,3R)-2-octadecanoylaminooctadecane-1,3-diol (component A), (2S,3R)-2-(2-hydroxyhexadecanoyl)aminooctadecane-1,3-diol (component B) and cholesterol, which includes a mixture of the above three components.

Confirmation of the formation of lamellar liquid crystal structure was carried out in accordance with the method of Mizushima et al. (Mizushima et al., *Oil Chemistry*, vol. 43, p. 656, 1994). In accordance with this method, association condition and phase behavior of the lipid composition were analyzed by a small angle X-ray diffractometer and a differential scanning calorimeter and observed under a polarization microscope.

The lipid composition can be used as a cosmetic or medicament by combining it with a cosmetic base or medicament base. As a preferable method for the preparation of such a product, a lipid composition formulated at a predetermined ratio is firstly dissolved by heating, and then a cosmetic base or medicament base is added to the dissolved composition or its paste after cooling.

The cosmetic or medicament mixed with the lipid composition of the invention can be prepared in the form of emulsion. Examples of the emulsion product include milky lotions and creams.

Amount of the lipid composition of the invention to be mixed with a cosmetic or medicament is not particularly limited. In the case of an emulsion, it is preferably from 0.001 to 10% by weight, more preferably from 0.02 to 3% by weight. The emulsion can have a water-in-oil or oil-in-water emulsion form. In this case, the oil phase is from 5 to 60% based on the total emulsion weight, the water phase is from 30 to 85% based on the total emulsion weight, and the emulsifying agent is from 1 to 20%, preferably from 2 to 12%, based on the total emulsion weight.

When the lipid composition of the invention is used in the preparation of products such as creams, lotions, ointments, shampoos, hair conditioners, rouges and foundations, it prevents transpiration of moisture from the skin by exerting its moisture-keeping function and barrier function, so that it can contribute to the improvement of dried skin and symptoms of atopic dermatitis.

Thus, since the lipid composition of the invention has high moisture-keeping and barrier functions, cosmetic compositions such as creams, emulsions and lotions prepared by formulating the lipid composition of the invention with other cosmetic bases can add moisture-keeping effect to the skin, improve affinity of moisture for the skin and add flexibility to the skin. In addition, since it also has dried or rough skin-preventing and improving effects, it shows excellent effects as external preparations for the skin, similar to those of cosmetic compositions.

Examples of the invention are given below by way of illustration but not by way of limitation.

EXAMPLE 1

Preparation of Lipid Compositions 1 to 6

Lipid compositions of the invention can be prepared by mixing the components (A), (B) and (C) at the respective weight ratio shown below. In the following examples, the racemic 2-acylaminoalkane-1,3-diol of the component (A) and its (2S,3R)-isomer were replaced by signs A and (2S,3R)-A, respectively, and (2S,3R)-isomer of the 2-acylaminoalkane-1,3-diol or 2-hydroxyacylaminoalkane-1,3-diol of the component (B) and its (2S,3R,2'R)-isomer were also replaced by signs (2S,3R)-B and (2S,3R,2'R)-B, respectively. The symbol C means cholesterol.

(Lipid composition 1); A ($R^1$ is $C_{15}H_{31}$, $R^2$ is $C_{17}H_{35}CO$):(2S,3R)-B ($R^1$ is $C_{15}H_{31}$, $R^3$ is $C_{14}H_{29}CH(OH)CO$):C=
(Lipid composition 2); A ($R^1$ is $C_{15}H_{31}$, $R^2$ is $C_{17}H_{35}CO$):(2S,3R)-B ($R^1$ is $C_{15}H_{31}$, $R^3$ is $C_{14}H_{29}CH(OH)CO$):C=9:1:10
(Lipid composition 3); (2S,3R)-A ($R^1$ is $C_{15}H_{31}$, $R^2$ is $C_{17}H_{35}CO$):(2S, 3R)-B ($R^1$ is $C_{15}H_{31}$, $R^3$ is $C_{14}H_{29}CH(OH)CO$):C=2:2:3
(Lipid composition 4); (2S, 3R)-A ($R^1$ is $C_{15}H_{31}$, $R^2$ is $C_{17}H_{35}CO$):(2S,3R)-B ($R^1$ is $C_{15}H_{31}$, $R^3$ is $C_{14}H_{29}CH(OH)CO$):C=9:1:10
(Lipid composition 5); (2S,3R)-A ($R^1$ is $C_{15}H_{31}$, $R^2$ is $C_{17}H_{35}CO$):(2S,3R,2R)-B ($R^1$ is $C_{15}H_{31}$, $R^3$ is $C_{14}H_{29}CH(OH)CO$):C=2:2:3
(Lipid composition 6); (2S,3R)-A ($R^1$ is $C_{15}H_{31}$, $R^2$ is $C_{17}H_{35}CO$):(2S,3R,2'R)-B ($R^1$ is $C_{15}H_{31}$, $R^3$ is $C_{14}H_{29}CH(OH)CO$):C=9:1:10

EXAMPLE 2

Confirmation of Lamellar Liquid Crystal Phase

Apparatus; Differential scanning calorimeter: DSC 220 (mfd. by Seiko Instrument Inc., to be referred to as DSC hereinafter)

Small angle X-ray diffractometer: PW 3050 (mfd. by Philips Japan Ltd.)

Polarization microscope: (mfd. by Olympus Optical Co.)

Each of the lipid compositions of the invention was completely dissolved in an appropriate amount of chloroform, and then chloroform was completely evaporated using an evaporator to obtain a powdery or paste solid. About 5 mg of the thus prepared sample was put into a sealable silver pan, and analyzed by DSC at a temperature rise/drop rate of 2° C./min.

In the case of the lipid compositions 1, 3, 5 and 7 shown in Example 1, when each lipid composition was melted by increasing the temperature to 150° C. and then the melted sample was cooled, each of the lipid compositions 1, 3, 5 and 7 caused exothermic reaction at around 108° C., at around 108° C., at around 105° C. or at around 106° C., respectively, while keeping a super-cooled liquid condition, and then transformed into liquid crystal state.

When the liquid crystal state was examined by X-ray diffractometer just after the formation of liquid crystal state and 14 days after the formation. Diffraction peaks were observed in the small angle region at Bragg spacing 41.8 Å (2θ=2.2°), 20.6 Å (2θ=4.3°), 13.4 Å (2θ=6.6°) and 10.2 Å (2θ=8.6°), their ratio was 1:1/2:1/3:1/4.

Also, since a blurred halo was observed at around 4.5 Å, it was confirmed that the thus obtained lipid compositions have a lamellar liquid crystal structure.

The liquid crystal state of each lipid composition shown in Example 1 was observed under polarizing microscope, analyzed the phase behavior by DSC and the structure by small angle X-ray diffractometer.

The result showed that these compositions formed lamellar liquid crystal structure and maintained this structure even after 14 days without crystallizing.

However, the lipid compositions of the invention are not limited to the above weight proportions. In order to form a desired lamellar liquid crystal structure, the components (A), (B) and (C) are mixed in the range defined in ternary phase equilibrium diagrams.

Figure 2:
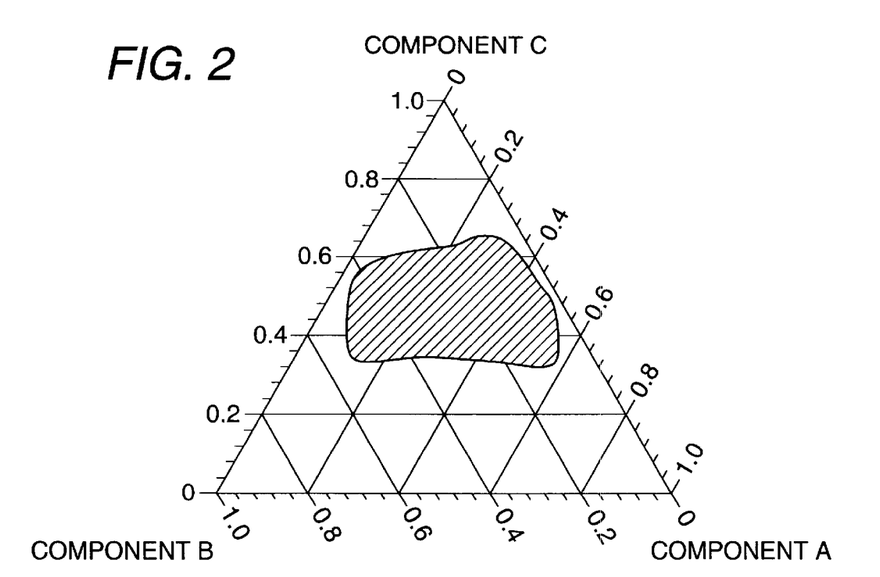
FIG. 2 is a graph showing a ternary phase equilibrium diagram comprised of (2S,3R)-2-octadecanoylaminooctadecane-1,3-diol (A), (2S,3R)-2-{(2R)-hydroxyhexadecanoyl}aminooctadecane-1,3-diol (B) and cholesterol (C).
Figure 3:
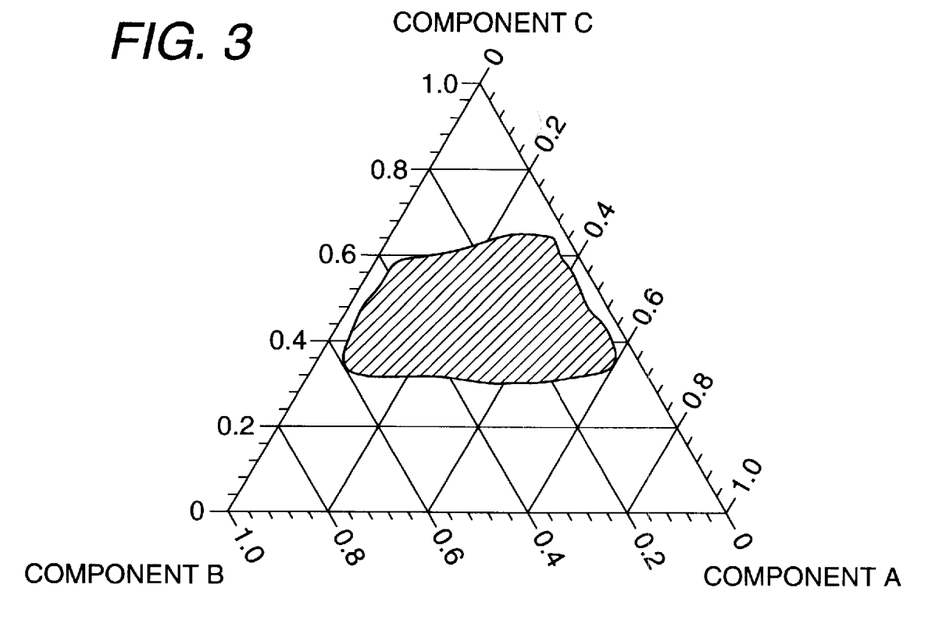
FIG. 3 is a graph showing a ternary phase equilibrium diagram comprised of racemic 2-octadecanoylaminooctadecane-1,3-diol (A), (2S,3R)-2-(2-hydroxyhexadecanoyl)aminooctadecane-1,3-diol (B) and cholesterol (C).

These diagrams shown in FIGS. 1 to 3, define preferable range of the components to be added to form lamellar liquid crystal phase.

FIG. 1 shows a ternary phase equilibrium diagram established using (2S,3R)-2-octadecanoylaminooctadecane-1,3-diol (A), (2S,3R)-2-(2-hydroxyhexadecanoyl) aminooctadecane-1,3-diol (B) and cholesterol (C).

FIG. 2 shows a ternary phase equilibrium diagram established using (2S,3R)-2-octadecanoylaminooctadecane-1,3-diol (A), (2S,3R,2'R)-2-(2'-hydroxyhexadecanoyl) aminooctadecane-1,3-diol (B) and cholesterol (C).

FIG. 3 shows a ternary phase equilibrium diagram established using racemic 2-octadecanoylaminooctadecane-1,3-diol (A), (2S,3R)-2-(2-hydroxyhexadecanoyl) aminooctadecane-1,3-diol (B) and cholesterol (C).

EXAMPLE 3

Comparison of Racemic Composition with Optically Active Composition)

Barrier Function Test 1

Method: Each of the lipid compositions 1, 3 and 5 was dissolved in chloroform to a concentration of 1% by weight, and No. 5C filter paper (mfd. by ADVANTEC) which had been cut off to the size of outer diameter of the mouth of SV-50 type sample bottle was soaked in the chloroform solution. Each of these filter papers was taken out and allowed to stand for 2 hours in an incubator set to a temperature of 60° C. to evaporate chloroform. Thereafter, each filter paper was put on the mouth of SV-50 type sample bottle containing 10 g of water, covered with the sample bottle cap having a bored hole of 24 mm in diameter and then allowed to stand for 48 hours in the incubator of 60° C. As a control, a filter paper prepared by soaking only in chloroform and then evaporating chloroform in the same manner was used. After 48 hours, the weight of these bottles (n=2) was measured to calculate the amount of transpired water and to obtain the barrier function (amount of transpired water per unit hour per unit area). Results of the comparison of in vitro barrier functions of respective lipid compositions are shown in Table 1.

TABLE 1

| Lipid Composition | Transpired water ($mg/cm^2/h$) |
|---|---|
| 1 | 8.35 |
| 3 | 7.15 |
| 5 | 7.48 |
| Control | 13.32 |

As can be seen from Table 1, it was found that the barrier function of lipid composition 3 was highest because of the smallest transpiration of water, and that of lipid composition 1 was lowest because of the largest transpiration.

So that it was clarified that lipid compositions formulated with optically active ceramides exhibited higher barrier function than that of racemic formulation.

In comparison of the barrier function with lipid compositions 3 and 5, the composition as component B formulated with (2S,3R)-2-(2-hydroxyhexadcanoyl)aminooctadecane-1,3-diol exhibited slightly higher than that formulated with (2S,3R,2'R)-2-(2'-hydroxyhexadecanoyl)aminooctadecane-1,3-diol (B).

Barrier Function Test 2

Method: Emulsion samples 1 to 5 were prepared by mixing the following components based on % by weight.

Sample 1: lipid composition 1 of the invention 16%, Decaglyn 1M(*) 16%, 1,3-butanediol 12%, concentrated glycerol 4%, purified water 52%

Sample 2: lipid composition 3 of the invention 16%, Decaglyn 1M 16%, 1,3-butanediol 12%, concentrated glycerol 4%, purified water 52%

Sample 3: lipid composition 5 of the invention 16%, Decaglyn 1M 16%, 1,3-butanediol 12%, concentrated glycerol 4%, purified water 52%

Sample 4: (2S,3R)-2-octadecanoylaminooctadecane-1,3-diol 16%, Decaglyn 1M 16%, 1,3-butanediol 12%, concentrated glycerol 4%, purified water 52%

Sample 5: (2S,3R,2'R)-2-(2'-hexadecanoyl)aminooctadecane-1,3-diol 16%, Decaglyn 1M 16%, 1,3-butanediol 12%, concentrated glycerol 4%, purified water 52%

Sample 6: Sarakosu HS(**) 16%, Decaglyn 1M 16%, 1,3-butanediol 12%, concentrated glycerol 4%, purified water 52% (*) Decaglyceryl monomyristate (commercial name by Nikko Chemicals Co., Ltd.) (**) Cholesteryl hydroxystearate (commercial name by Nisshin Oil Mills Ltd.)

In this case, the samples 4 and 5 are control emulsions in which a ceramide alone is formulated, and the sample 6 is a control emulsion in which ceramide is not formulated.

Each of the samples 1 to 6 was uniformly coated on the No. 5C filter paper which had been cut off to the size of outer diameter of the mouth of SV-50 type sample bottle, in an amount of from 40 to 60 mg, and then dried in an incubator at a temperature of 40° C. and under a relative humidity of 15% or less for 2 hours. Thereafter, each of the dried filter papers was put on the mouth of SV-50 type sample bottle containing 10 g of water, covered with the sample bottle cap having a bored hole of 24 mm in diameter and then allowed to stand for 96 hours in the incubator. As a control, a dried filter paper without sample coating was employed and the same treatment was carried out. After 96 hours of the standing, the weight of each sample bottle was measured to calculate the barrier function of each sample from the amount of reduced weight in the same manner as the case of the test 1. Results of the comparison of in vitro barrier functions of respective samples formulated with various lipid compositions are shown in Table 2.

TABLE 2

| Sample | Amount of transpired water (mg/cm$^2$/h) |
|---|---|
| 1 | 5.25 |
| 2 | 2.91 |
| 3 | 3.48 |
| 4 | 6.77 |
| 5 | 6.75 |
| 6 | 6.63 |
| Control | 12.25 |

As shown in Table 2, it was also found that the sample 2, formulated with lipid composition 3, exhibited the highest barrier function because of the smallest transpiration of water.

It was the same result as Example 3 that samples 1 and 3, the lipid compositions of which were formulated either with racemic ceramides or with (2S,3R, 2'R)-2-(2'-hydroxyhexadecanoyl)aminooctadecane-1,3-diol as component B, were exhibited rather low barrier functions than sample 1, the lipid composition of which was formulated with (2S,3R)-2-(2-hydroxyhexadecanoyl)aminooctadecane-1,3-diol as component B. The samples 4 and 5 which each ceramide alone was formulated, were exhibited lower barrier function.

EXAMPLE 4 AND COMPARATIVE EXAMPLE 2

Comparison with Conventional Lipid Compositions

In accordance with the method described in Example 3 (comparison of racemic composition with optically active composition), emulsion samples were prepared from the following lipid compositions, and the barrier function of each sample was compared with that of the emulsion sample 2 prepared from the lipid composition 3. The compositional ratio was shown by weight ratio.

(Lipid composition 7): (2S,3R)-2-acetaminooctadecane-1,3-diol (D):(2S,3R)-2-octadecanoylaminooctadecane-1,3-diol (A):cholesteryl hydroxystearate (E):cholesterol (C)= 1:2:1:2

(Lipid composition 8): pseudo ceramide (F):stearic acid (G):cholesterol (C):cholesteryl isostearate (H):=10:6:3:1 (wherein the pseudo ceramide means N-(3-hexadecyloxy-2-hydroxypropyl)-N-2-hydroxyethylhexadecamide)

Using these two lipid compositions, emulsion samples 7 and 8 were prepared in the same manner as the case of Example 3.

Sample 7: lipid composition 7 16%, Decaglyn 1M 16%, 1,3-butanediol 12%, concentrated glycerol 4%, purified water 52%

Sample 8: lipid composition 8 16%, Decaglyn 1M 16%, 1,3-butanediol 12%, concentrated glycerol 4%, purified water 52%

Barrier functions of samples 7 and 8 were compared with sample 2 described in Example 3, in the same manner as Example 3.

As shown in Table 3, sample 2 was exhibited higher barrier function than samples 7 and 8.

As the results of barrier function tests in vitro, lipid composition of this invention formulated with (2S,3R)-2-oxtadecanoylaminooctadecane-1,3-diol, (2S,3R)-2-(2-hydroxyhexadecanoyl)aminooctadecane-1,3-diol and cholesterol, the compositional weight ratio of which was 2:2:3, exhibited highest barrier functions, either in state of lipid composition or in state of emulsion.

TABLE 3

| Sample | Amount of transpired water (mg/cm$^2$/h) |
|---|---|
| 2 | 3.17 |
| 7 | 4.56 |
| 8 | 3.83 |

As a result of the barrier function testing, it was revealed that the barrier function of sample 2 is larger than the barrier function of samples 7 and 8, namely, the barrier function of emulsion containing (2S,3R)-2-octadecanoylaminooctadecane-1,3-diol, (2S,3R)-2-(2-hydroxyhexadecanoylamino)-1,3-diol and cholesterol as the lipid composition is larger than the barrier function of emulsions prepared using conventional lipid compositions.

EXAMPLE 5

Preparation of Creams

The lipid composition 3 or 4 was added to the oil phase of the following formulation and dissolved therein with heating (A phase). The B phase was uniformly dissolved, mixed with the C phase and kept at 80° C. and then mixed with the A phase and vigorously stirred using a homogenizer, and the mixture thus obtained was cooled to 45° C., mixed with the D phase, homogenized by stirring and then cooled to room temperature, thereby preparing creams.

| Formulation | % by weight |
|---|---|
| A phase: | |
| Lipid composition 3 or 4 | 1.0 |
| Polyoxyethylene sorbitan monostearate (20 E.O.) | 1.7 |
| Self emulsification type glycerol monostearate | 3.0 |
| Stearic acid | 1.0 |
| Bleached beeswax | 2.5 |
| Cetyl palmitate | 2.0 |
| Behenyl alcohol | 0.5 |
| Polyoxyethylene sorbitol beeswax (6 E.O.) | 0.5 |
| Glyceryl tri-2-ethylhexanoate | 5.0 |
| Squalane | 10.0 |
| Butylparaben | 0.1 |
| B phase: | |
| Purified water | 68.27 |
| Carboxyvinyl polymer | 0.1 |
| 1,3-Butylene glycol | 3.0 |
| Methylparaben | 0.2 |
| C phase: | |
| purified water | 1.0 |
| Sodium hydroxide | 0.03 |
| D phase: | |
| Perfume | 0.1 |

EXAMPLE 6

Preparation of Lotions

The lipid composition 4 or 5 was added to the oil phase of the following formulation and uniformly dissolved therein with heating (A phase), mixed with the B phase which had been heated at 80° C. and then vigorously stirred using a homogenizer, and the emulsion thus obtained was cooled to 45° C., mixed with the C phase and then cooled to room temperature, thereby preparing lotions.

| Formulation | % by weight |
|---|---|
| A phase: | |
| Lipid composition 4 or 5 | 1.0 |
| Decaglyceryl monomyristate | 1.0 |
| Concentrated glycerol | 2.0 |
| 1,3-Butylene glycol | 2.0 |
| Methylparaben | 0.1 |
| B phase: | |
| purified water | 93.88 |
| C phase: | |
| Perfume | 0.02 |

EXAMPLE 7

Preparation of Emulsions

The lipid composition 5 or 6 was added to the oil phase of the following formulation and uniformly dissolved therein with heating (A phase). The B phase was uniformly dissolved, mixed with the C phase and kept at 80° C. and then mixed with the A phase and stirred using a homogenizer, and the emulsion thus obtained was cooled to 45° C., mixed with the D phase and then homogenized by stirring, thereby preparing emulsions.

| Formulation | % by weight |
|---|---|
| A phase: | |
| Lipid composition 5 or 6 | 1.0 |
| Concentrated glycerol | 3.0 |
| Squalane | 5.0 |
| Glyceryl tri-2-ethylhexanoate | 5.0 |
| Decaglyceryl monomyristate | 2.0 |
| Behenyl alcohol | 1.0 |
| Lipophilic glyceryl monostearate | 0.5 |
| Cetyl palmitate | 0.5 |
| Stearic acid | 0.5 |
| Propylparaben | 0.1 |
| B phase: | |
| Purified water | 78.07 |
| Carboxyvinyl polymer | 0.1 |
| 1,3-Butylene glycol | 2.0 |
| Methylparben | 0.1 |
| C phase: | |
| purified water | 1.0 |
| Sodium hydroxide | 0.03 |
| D phase: | |
| Perfume | 0.1 |

EXAMPLE 8

Preparation of Rouges

The lipid composition 3 or 4 was added to the following formulation, dissolved therein with heating and then cooled, thereby preparing rouges.

| Formulation | % by weight |
|---|---|
| Lipid composition 3 or 4 | 1.0 |
| Beeswax | 28.0 |
| Ceresin | 5.0 |
| Candelilla wax | 5.0 |
| Castor oil | 30.0 |
| Lanolin | 5.0 |
| Cacao butter | 10.0 |
| Glyceryl monostearate | 3.0 |
| Liquid paraffin | 5.0 |
| Bromic acid | 1.0 |
| Lake (coloring agent) | 6.5 |
| Perfume | 0.5 |

EXAMPLE 9

Preparation of Hydrophilic Ointments

The lipid composition 4 or 5 was added to the oil phase of the following formulation and uniformly dissolved therein with heating (A phase). The B phase was uniformly dissolved, kept at 80° C., mixed with the A phase and then stirred and homogenized, thereby preparing hydrophilic ointments.

| Formulation | % by weight |
|---|---|
| A phase: | |
| Lipid composition 4 or 5 | 3.0 |
| Polyoxyethylene cetyl ether | 2.0 |
| Self emulsification type glycerol monostearate | 10.0 |
| Liquid paraffin | 10.0 |
| Vaseline | 5.0 |
| Cetanol | 6.0 |
| Propylene glycol | 9.0 |
| B phase: | |
| Propylene glycol | 1.0 |
| Purified water | 53.9 |
| Methylparaben | 0.1 |

EXAMPLE 10

Preparation of Oil Ointments

The lipid composition 3 or 4 was added to the following formulation, uniformly dissolved therein with heating and then cooled, thereby preparing oily ointments.

| Formulation | % by weight |
|---|---|
| Lipid composition 3 or 4 | 3.0 |
| Liquid paraffin | 38.8 |
| Vaseline | 58.2 |

EXAMPLE 11

The creams of Example 5 formulated with the lipid composition 3 (to be referred to as cream 1), creams not containing the lipid composition (to be referred to as blank hereinafter) and, as a comparative example, creams containing (2S,3R)-2-octadecanoylaminooctadecane-1,3-diol (ceramide 2) or (2S,3R,2'R)-2-(2'-hydroxyhexadecanoyl) aminooctadecane-1,3-diol (ceramide 5) were prepared by the following formulation (to be referred to as cream 2 and cream 3, respectively). These creams were prepared in accordance with the method of Example 5, and 69.27% by weight of purified water was used in the case of the blank (cream 4).

| Formulation | % by weight |
|---|---|
| A phase: | |
| Ceramide 2 or 5 | 0.6 |
| Cholesterol | 0.4 |
| Polyoxyethylene sorbitan monostearate (20 E.O.) | 1.7 |
| Self emulsification type glycerol monostearate | 3.0 |
| Stearic acid | 1.0 |
| Bleached beeswax | 2.5 |
| Cetyl palmitate | 2.0 |
| Behenyl alcohol | 0.5 |
| Polyoxyethylene sorbitol beeswax (6 E.O.) | 0.5 |
| Glyceryl tri-2-ethyihexanoate | 5.0 |
| Squalane | 10.0 |
| Butylparaben | 0.1 |

-continued

| Formulation | % by weight |
|---|---|
| B phase: | |
| Purified water | 68.27 |
| Carboxyvinyl polymer | 0.1 |
| 1,3-Butylene glycol | 3.0 |
| Methylparaben | 0.2 |
| C phase: | |
| purified water | 1.0 |
| Sodium hydroxide | 0.03 |
| D phase: | |
| Perfume | 0.1 |

Evaluation of these creams was carried out by a panel of 15 women of from 23 to 54 years old having relatively dried skin. This evaluation was carried out during a relatively dry season of from November to the following February.

Each of the cream samples was applied to 4 predetermined positions on the forearms of both arms once or twice a day for 20 days continuously, and spreading of the cream during the test period, feeling of moistness or softness of the skin during and after the test period and general feeling during the test period were compared based on the following evaluation criteria and the results were judged by their average points.

| [Evaluation] | [Judgment (average point)] |
|---|---|
| 5 points: very good | ⊙⊙: 4.5 or more |
| 4 points: good | ⊙: 3.5 or more and less than 4.5 |
| 3 points: common | Δ: 2.5 or more and less than 3.5 |
| 2 points: slightly poor | X: less than 2.5 |
| 1 point: poor | |

The thus obtained results are shown in Table 4. The symbols c.1, c.2, c.3 and c.4 indicate cream 1, cream 2, cream 3 and cream 4, respectively.

TABLE 4

| Items (used feeling) | c.1 | c.2 | c.3 | c.4 |
|---|---|---|---|---|
| Spreading of the cream | ⊙⊙ | ⊙ | Δ | X |
| Moistness, softness | ⊙⊙ | ⊙ | ⊙ | Δ |
| General used feeling | ⊙⊙ | ⊙ | ⊙ | Δ |

As is evident from the results shown in Table 4, the cream 1 formulated with the lipid composition 3 of the invention showed the best spreading and the most excellent feeling of moistness and softness of the skin, and also the best general feeling among the creams tested.

While the invention has been described in detail and with reference to specific embodiments thereof, it will be apparent to one skilled in the art that various changes and modifications can be made therein without departing from the spirit and scope thereof.

This application is based on Japanese patent applications No. 2000-169104 filed on Jun. 6, 2000, the entire contents thereof being hereby incorporated by reference.

What is claimed is:

1. A lipid which comprises (1) at least one component (A) selected from the group consisting of a 2-acylaminoalkane-1,3-diol represented by a general formula (I)

(I)

wherein $R^1$ represents a straight chain alkyl group having from 9 to 17 carbon atoms and $R^2$ represents a straight chain acyl group having from 14 to 24 carbon atoms and optically active compounds thereof, (2) at least one component (B) selected from the group consisting of a 2-acylaminoalkane-1,3-diol represented by a general formula (II)

(II)

wherein $R^1$ represents a straight chain alkyl group having from 9 to 17 carbon atoms and $R^3$ represents a straight chain acyl group having from 2 to 24 carbon atoms in which at least one of the α-position and β-position is substituted with hydroxyl group and optically active compounds thereof and (3) at least one component (C) selected from at least one sterol, wherein the components (A), (B) and (C) are mixed at a ratio that constructs a liquid crystal structures, wherein compositional ratios (weight ratios) of the component (A) to component (B), component (B) to component (C) and component (A) to component (C) are from 1:9 to 9:1, from 9:6 to 1:10 and from 1:1 to 1:9, respectively.

2. The lipid composition having a liquid crystal structure according to claim 1, wherein the at least one sterol of component (C) is cholesterol, coprostanol, sitosterol, stigmasterol or ergosterol.

3. The lipid composition having a liquid crystal structure according to claim 1, wherein $R^3$ of the general formula (II) is 2-acylaminoalkane-1,3-diol having a straight chain acyl group having from 2 to 24 carbon atoms in which the α-position or β-position is substituted with hydroxyl group.

4. The lipid composition having a liquid crystal structure according to claim 1, wherein the component (A) is a (2S,3R)-2-acylaminoalkane-1,3-diol represented by a general formula (III)

(III)

wherein $R^1$ and $R^2$ are as defined in the foregoing.

5. The lipid composition having a liquid crystal structure according to claim 1, wherein the component (B) is a (2S,3R)-2-acylaminoalkane-1,3-diol represented by a general formula (IV)

(IV)

wherein $R^1$ and $R^3$ are as defined in the foregoing.

6. A cosmetic or medicament which comprises the lipid composition defined in any one of claims 1 to 5 containing a pharmaceutically acceptable base material as an additional component.

* * * * *